(12) United States Patent
Korotkov et al.

(10) Patent No.: US 8,321,010 B2
(45) Date of Patent: Nov. 27, 2012

(54) METHOD FOR DETERMINING THE CONDITION OF A BIOLOGICAL OBJECT AND DEVICE FOR MAKING SAME

(76) Inventors: Konstantin Georgievich Korotkov, Saint Petersburg (RU); Ramiz Ragim-Ogly Yusubov, Saint Petersburg (RU)

( * ) Notice: Subject to any disclaimer, the term of this patent is extended or adjusted under 35 U.S.C. 154(b) by 0 days.

(21) Appl. No.: 13/146,860

(22) PCT Filed: Sep. 4, 2009

(86) PCT No.: PCT/RU2009/000460
§ 371 (c)(1),
(2), (4) Date: Jul. 28, 2011

(87) PCT Pub. No.: WO2011/028146
PCT Pub. Date: Mar. 10, 2011

(65) Prior Publication Data
US 2011/0282214 A1    Nov. 17, 2011

(51) Int. Cl.
*A61N 1/30* (2006.01)
(52) U.S. Cl. .............. 604/20; 604/23; 604/26; 600/473; 600/476
(58) Field of Classification Search .......... 600/407–429, 600/473–480; 604/20–26
See application file for complete search history.

(56) References Cited

U.S. PATENT DOCUMENTS

| | | | |
|---|---|---|---|
| 4,168,522 A * | 9/1979 | van de Laarschot et al. | 362/294 |
| 6,835,202 B2 * | 12/2004 | Harth et al. | 607/91 |
| 6,888,301 B1 * | 5/2005 | Namiki et al. | 313/489 |
| 7,329,981 B2 * | 2/2008 | Nakao et al. | 313/478 |
| 7,916,291 B2 * | 3/2011 | Milster et al. | 356/301 |
| 2002/0128695 A1 * | 9/2002 | Harth et al. | 607/88 |
| 2007/0222712 A1 * | 9/2007 | Chiaki et al. | 345/63 |
| 2009/0168152 A1 * | 7/2009 | Gelernt et al. | 359/353 |
| 2010/0053599 A1 * | 3/2010 | Milster et al. | 356/51 |
| 2010/0194288 A1 * | 8/2010 | Norgaard | 315/149 |
| 2011/0021970 A1 * | 1/2011 | Vo-Dinh et al. | 604/20 |
| 2011/0025187 A1 * | 2/2011 | Tews et al. | 313/487 |

\* cited by examiner

*Primary Examiner* — Sanjay Cattungal
(74) *Attorney, Agent, or Firm* — John D. Gugliotta, Esq.; Nicholas A. Mihalic, Esq.; Howard L. Wernow

(57) ABSTRACT

The invention relates to the field of instrumentation and can be used for diagnosing the condition of a biological object. The technical result consists in an increased measurement precision. In order to achieve this result, the invention comprises determining the condition of a biological object on the basis of fixation and comparison of the structures of gas-discharge light emission around the reference object and the biological object under study in an electromagnetic field. The light emissions around the reference object and the biological object under study are converted into digital code. The invention comprises determining the quantitative parameters of the light emission and the characteristics thereof. The invention also comprises determining corresponding spatial points of specified parameters for the reference object and the biological object under study. The invention further comprises determining the deviation of quantitative parameters that characterize the condition of the biological object under study by means of the distance between said points. The reference object is implemented as a non-biological material. The invention also comprises carrying out the fixation of the structure of gas-discharge light emission around the reference object and determining the relative deviation thereof from an average value.

5 Claims, 3 Drawing Sheets

METHOD FOR DETERMINING THE CONDITION OF A BIOLOGICAL OBJECT AND DEVICE FOR MAKING SAME

TECHNICAL FIELD

The inventions relate to the field of physics and can be used for determining the functional condition of a biological object.

BACKGROUND ART

A known method for determining the condition of a biological object, in particular a human, comprises fixation and comparison of the structure of gas-discharge light emission in an electric field around the whole reference object or a part thereof (fingertips) at the initial level (outside the vegetovascular crisis) and prior to the crisis, see SU 935076 A1.

Reference data used in this method can be embodied not only as the initial level of gas-discharge light emission around the tested object outside of the crisis condition, but also as the level of gas-discharge light emission around an undoubtedly healthy biological object that is taken as a reference object.

During implementation of this method quantitative criteria are introduced for evaluating the condition of a biological object, allowing to compare the object's condition at different points of time or to compare the condition of different objects.

However, such method does not provide sufficient accuracy and reliability in determining the biological object's condition, because it takes into account only one parameter of the glow structure, namely the length of the gas-discharge streamer. In addition, it should be noted that the process of obtaining the information is quite labor-intensive and lengthy: one must obtain the photographic images, measure them with common measuring tools and then compare the measurement results. Another disadvantage of this method consists in the fact that assessment of a biological object's condition is performed within a fairly narrow range of variations of a one-dimensional geometrical parameter—the streamer length (from 15 to 30% as compared to the initial level). In addition, the object's condition cannot be assessed if the changes of said parameter fall outside the described limits.

Higher precision and reliability of assessment of the condition of a biological object within a wide range of values of quantitative parameters that characterize the structure of gas-discharge light emission around objects in a electromagnetic field is provided by a method for determining the condition of a biological object by means of fixation and comparison of the structure of gas-discharge light emission around the reference object and the object under study in an electromagnetic field, which comprises converting fixed structures of gas-discharge light emission around the reference object and the test object into digital code, determining quantitative parameters of said structures that reflect their characteristics, determining corresponding spatial points of said parameters for the reference and the test objects, and then determining the deviation of the test object from the reference object according to the distance between said points; in addition, the method may comprise determining the quantitative parameters of the structures of gas-discharge light emission that reflect their spectral, brightness and fractal characteristics, wherein the abovementioned points in a multidimensional space are determined taking into account these parameters as well, see RU 2141250 C1.

This method has been taken as a prototype of the present inventive method.

In the prototype method the reference object is embodied as a finger of a person considered to be healthy. However, any biological object has a particular dynamics of biological parameters that characterize its condition, and this dynamics depends on the temporal, climatic, geophysical and other factors acting at the place of the experiment. Therefore the prototype method uses for comparison a metrological basis that is essentially an insufficiently stable biological object, which leads to a certain inaccuracy of determination of the condition of the biological object under study.

The same patent RU 2141250 C1 describes a device for determining the condition of a biological object that comprises an electromagnetic pulse generator, a glass plate that has an electrode on the lower surface thereof in the form of a thin layer of a conductive optically transparent material, an objective lens, an optoelectronic digital converter (OEDC), a computer unit in the form of a personal computer and an information presentation unit in the form of a monitor; one output of the generator is connected to the electrode and the second output of the generator is connected to a switching device which is in turn connected to the reference or the test object, ensuring alternating contact with said objects; the output of the objective lens is optically connected to the optical input of the OEDC, the output of which is connected to the input of the computer unit, the output of which is connected to the input of the information presentation unit (monitor).

This device was taken as a prototype of the inventive device according to the present patent application.

The prototype device can be used for determining the condition of a biological object by means of fixation and comparison of the structures of gas-discharge light emission around the reference object and the biological object under study only when the reference object is embodied as a biological object, which, due to the reasons described above in the description of corresponding known method, does not provide sufficient and (in some cases) necessary accuracy of determination of the biological object's condition during fixation and comparison of the structures of gas-discharge light emission around the reference and the test objects. It should be mentioned that the prototype device does not allow using an object made of a non-biological material as a metrological basis for such comparison, because it does not allow correcting the relative deviation $\delta$ of a value in the series of measured quantitative parameters of structures of gas-discharge light emission around the reference object from their average value, which is necessary when using a reference object made of a non-biological material, since in this case the values of $\delta$ can be significantly larger than the allowed value of variability of measured parameters that is accepted during the biomedical measurements—not more than 10%. When this limit is surpassed, the biomedical measurements are considered invalid.

SUMMARY OF THE INVENTIONS

The present inventions provide a solution that increases the accuracy of determining the condition of a biological object.

In order to obtain said technical result, the inventive method for determining the condition of a biological object by means of fixation and comparison of the structures of gas-discharge light emission around the reference object and the object under study in an electromagnetic field, which is created by an electromagnetic pulse generator, comprises converting fixed structures of gas-discharge light emission around the reference object and the test biological object into digital code, determining quantitative parameters of said structures that reflect their characteristics, determining corresponding spatial points of said parameters for the reference object and the test biological object, and then using the distance between said points to determine the deviation of quantitative parameters that characterize the condition of the biological object under study from the quantitative parameters that characterize the reference object, wherein the novel features consist in that the reference object used in the method is made of a non-biological material, the fixation of the structure of gas-discharge light emission around the reference object is performed multiple times, the relative deviation δ of a value in the series of measured quantitative parameters of structures of gas-discharge light emission around the reference object from their average value is calculated, and at δ≦10% the structures of gas-discharge light emission around the reference and the test biological objects are compared, whereas at δ>10% the output voltage of the electric pulse generator is reduced and/or the stability of said pulses is increased until obtaining δ≦10%; it is possible to use a reference object made of metal; it is possible to use a reference object in the form of a vessel containing conductive liquid.

In order to obtain said technical result, the inventive device for determining the condition of a biological object comprises an electromagnetic pulse generator, a glass plate that has an electrode on the lower surface thereof in the form of a layer of a conductive optically transparent material, an objective lens, an optoelectronic digital converter, a computer unit, an information presentation unit, a switching device that allows connecting the generator in turn to the reference object or the biological object under study, wherein the first output of the generator is connected to the switching device and the second output of the generator is connected to the electrode, the output of the objective lens is optically connected to the optical input of the optoelectronic digital converter, and the first output of the computer unit is connected to the input of the information presentation unit, wherein the novel features consist in that the device additionally comprises a unit for calculating the relative deviation δ of a value in the series of measured quantitative parameters of structures of gas-discharge light emission around the reference object from their average value and a unit of logical decisions, wherein the input of the unit for calculating the relative deviation δ is connected to the first output of the optoelectronic digital converter, the second output of which is connected to the first input of the computer unit, the second input of which is connected to the first output of the unit of logical decisions, the second output of which is connected to the generator input; the switching device can be embodied as an electronic or electromechanical switch.

The applicant has not found any sources of information containing data on engineering solutions identical to the inventive method and the device for implementation thereof, which enables to conclude that the inventive method and the inventive device conform to the criterion "Novelty" (N).

Realization of the features of the inventive method provide the object with an important new property that consists in that the condition of a biological object is determined in comparison with an object, parameters of which do not depend on the influence of temporal, climatic, geophysical and other factors, thus ensuring an increased accuracy of determination of the condition of the biological object under study. Realization of the features of the inventive device allows using a non-biological object as a reference object. In applicant's opinion, these facts enable to conclude that the method and device according to the present application conform to the criterion "Inventive Step" (IS).

BRIEF DESCRIPTION OF THE DRAWINGS

The inventions are further explained, by way of example, with reference to the following drawings, in which.

PREFERRED EMBODIMENT

Figure 1:
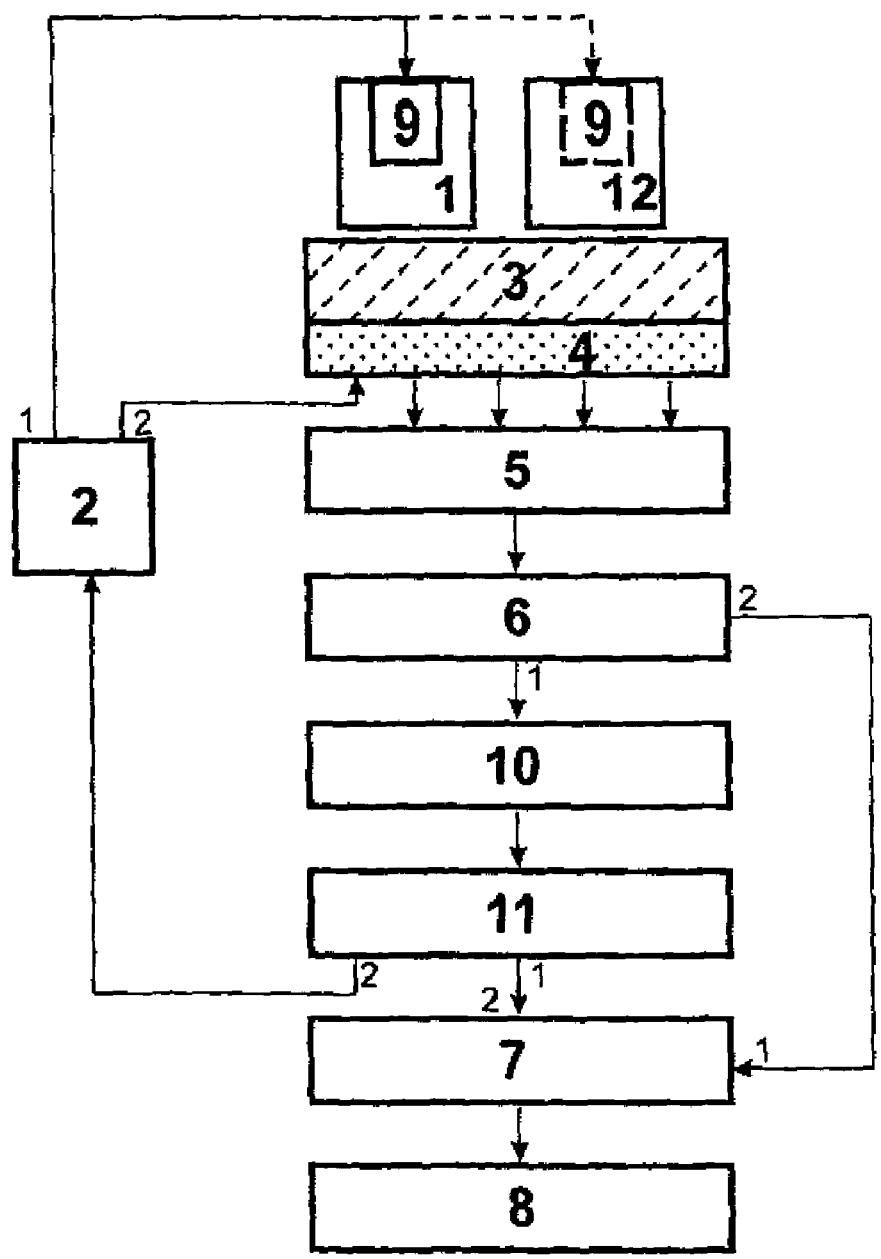
FIG. 1—schematic of the device for implementation of the inventive method, in which:
  1—biological object under study;
  2—generator of electric pulses;
  3—glass plate;
  4—electrode;
  5—objective lens;
  6—optoelectronic digital converter;
  7—computer unit;
  8—information presentation unit;
  9—switching device for connecting the generator in turn to the reference object or the biological object under study;
  10—unit for calculating the relative deviation;
  11—unit of logical decisions;
  12—reference object.

The inventive device for determining the condition of a biological object 1 comprises a generator 2 of electromagnetic pulses with pulse height of 3-5 kV, duration of 10 µsec and ratio of 1000 Hz, which are supplied in bursts with duration of 0.5 sec. In this particular embodiment the generator of electric pulses is embodied as GDV Camera manufactured by company Kirlionics Technologies International (St. Petersburg, Russia). The lower surface of glass plate 3 has an electrode 4 in the form of a layer of conductive optically transparent material, in this particular embodiment a layer of $SnO_2$ with thickness of 200 µm or a layer of Ag with thickness of 10 µm. Output of objective lens 5 is optically connected to the optical input of the EODC 6, which is a matrix structure embodied on the basis of a device with charge coupling (the so-called CCD structure). The computer unit 7 is embodied in this particular example as a controller ATmega 16 manufactured by company ATMEL (USA), the information presentation unit 8 is a monitor by LG, FLATRON, L17308, the input of which is connected to the first output of the unit 7. Switching device 9 is embodied so as to allow alternating connection of the generator 2 to the reference object 12 or the biological object under study 1 and can be in the form of a spring-loaded crocodile clip, like in the example according to claim 4 (see FIG. 1), which is electrically connected to the first output of generator 2. In the example according to claim 5 the switching device 9 is embodied as an electronic switch (in particular, a trigger) or an electromechanical switch (in particular, a relay). In this case the switching device is also electrically connected (with its first input) to the first output of the generator, and is also connected with its second input to the second output of the computer unit 7. Similarly to the example in FIG. 1, the switching device in turn connects the first output of generator 2 either to the tested biological object 1 or to the reference object 12, which is embodied as a metal cylinder, in particular made of copper or titanium; it is possible to use a vessel with conductive liquid as a reference object, in particular a vessel with NaCl solution. In this case the electric contact can take place directly with the conductive liquid. The device also comprises a unit 10 for calculating the relative deviation δ of values in the series of measured quantitative parameters of the structure of gas-discharge light emission around the reference object 12 from their average value, and a unit 11 of logical decisions. Units 10 and 11 in this particular example are embodied as controllers ATmega 16 manufactured by company ATMEL (USA). The input of unit 10 is connected to the first output of the OEDC 6, the second output of which is connected to the first input of the computer unit 7, the second input of which is connected to the first output of the unit 11 of logical decisions, the second output of which is connected to the input of generator 2.

Figure 2:
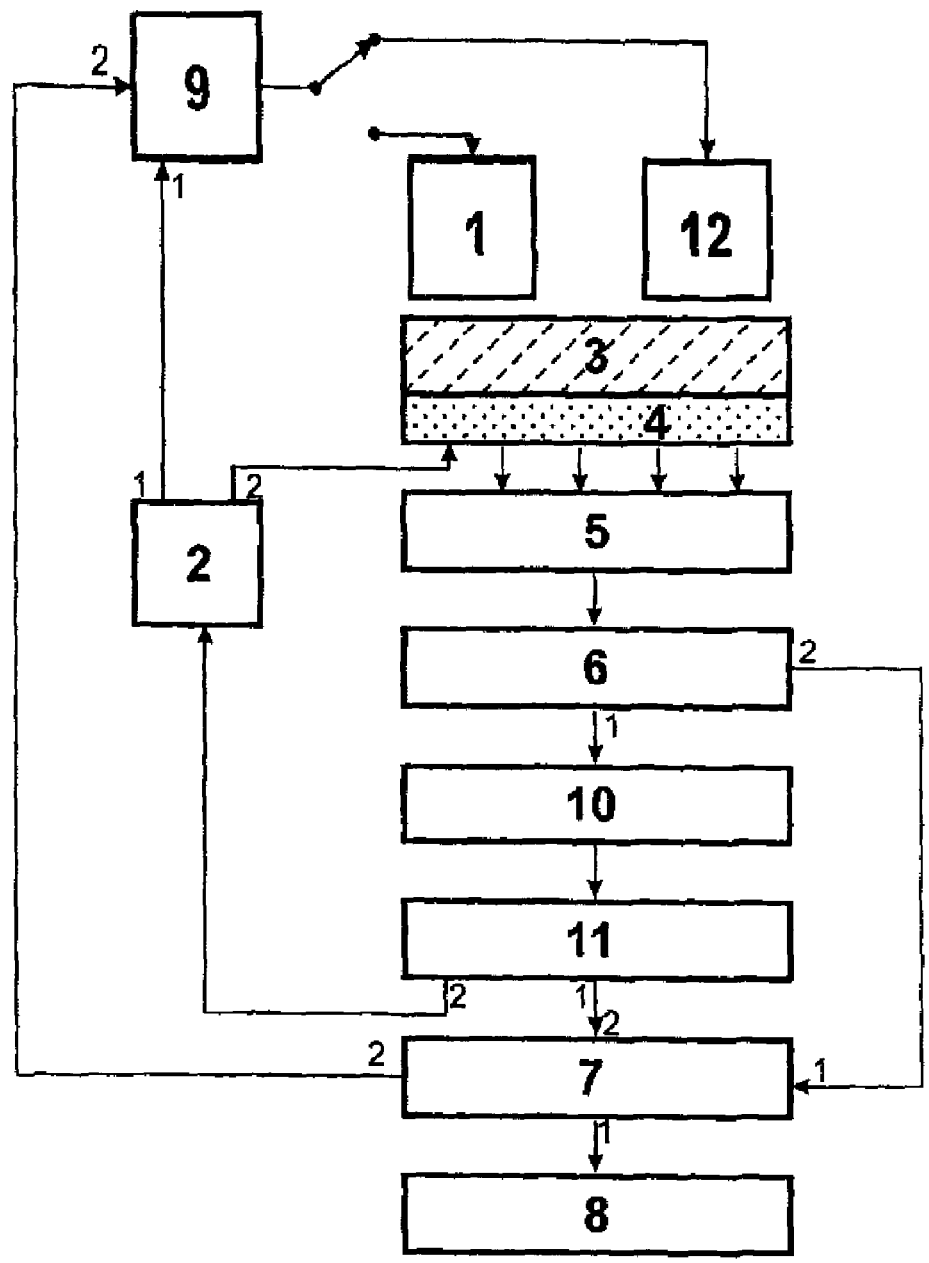
FIG. 2—same as FIG. 1, where the switching device is embodied as an electronic or electromechanical switch.

The inventive method is implemented by means of the inventive device in the following way. The reference object 12 is brought into contact with the surface of the glass plate 3. Here the first output of generator 2 is connected to the reference object 12 by means of switching device 9 (a resettable clip shown with dotted line in FIG. 1) or an electronic (electromechanical) switch (see FIG. 2). Electromagnetic field created by means of generator 2 produces gas-discharge light emission around the reference object 12. This light emission is transferred by means of the objective lens 5 to the OEDC 6, which converts it into digital code. From the output of the OEDC 6 the signal goes to the input of the computer unit 7, where the quantitative parameters of the structure of gas-discharge light emission around the reference object 12 are determined. Fixation of the structure of gas-discharge light emission around the reference object and the measurement of quantitative parameters of this structure are performed multiple times. Then the unit 10 is used for calculating the relative deviation $\delta$ of values in the series of measured quantitative parameters of the structure of gas-discharge light emission around the reference object 12 from their average value. When $\delta > 10\%$, the unit 10 sends a signal to the unit 11 of logical decisions, which controls the generator 2, reducing its output voltage and/or increasing the stability of the pulses until obtaining $\delta \leq 10\%$. Unit 7 is used for determining the spatial point of specified parameters for the reference object 12. When $\delta \leq 10\%$, the reference object 12 is brought out of contact with the glass plate 3, the generator 2 is connected to the biological object under study 1 and then the biological object 1 is brought into contact with the glass plate 3. The quantitative parameters of the light emission structure, which reflect the characteristics of the biological object under study 1, are determined, and then the spatial point in the field of said parameters is determined by means of unit 7.

Figure 3:
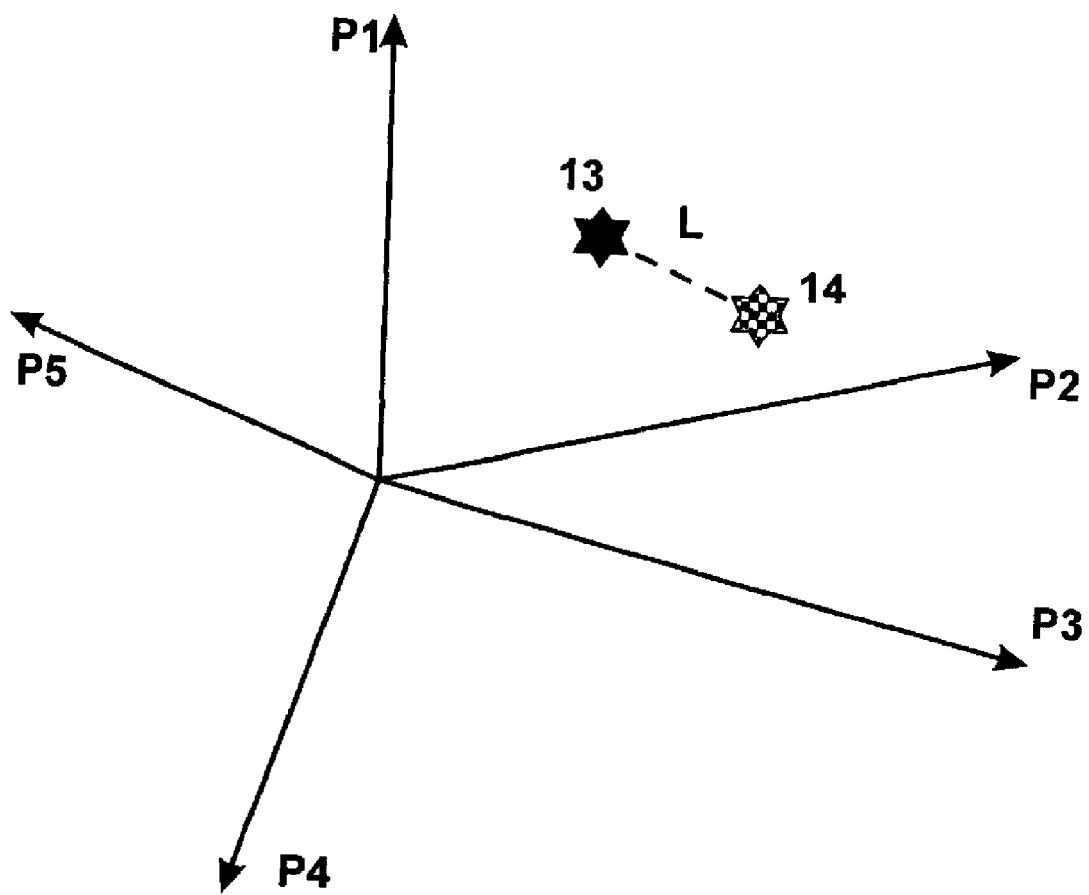
FIG. 3—points in a multi-dimensional space of quantitative parameters of the structures of gas-discharge light emission around the reference and the test objects that reflect their characteristics.

Then the distance between corresponding points (like in the prototype) is used for determining the deviation of quantitative parameters that characterize the condition of the biological object under study from the quantitative parameters that characterize the reference object. In this particular example (FIG. 3) the axes P1 and P2 correspond to the quantitative parameters of the light emission structures that reflect their two-dimensional geometrical characteristics, the axis P3 corresponds to the quantitative parameters that reflect the brightness characteristics of the light emission structures, the axis P4 reflects their spectral characteristics, and the axis P5—their fractal characteristics. Point 13 in a multi-dimensional space of axes P1, P2, P3, P4 and P5 corresponds to the reference object 12. Point 14 in the multi-dimensional space that corresponds to the object under study 1 is determined in the same way. Then the condition of the object under study is determined on the basis of the distance L between points 13 and 14.

Industrial Applicability

The inventive method can be implemented by means of common constructional materials and industrial equipment that is manufactured in factory conditions. This enables to conclude that the invention conforms to the criterion "Industrial Applicability" (IA).

The invention claimed is:

1. A method for determining the condition of a biological object by means of fixation and comparison of the structures of gas-discharge light emission around the reference object and the biological object under study in an electromagnetic field created by an electromagnetic pulse generator, which comprises converting fixed structures of gas-discharge light emission around the reference object and the biological object under study into digital code, determining quantitative parameters of said glow structures that reflect their characteristics, determining corresponding spatial points of said parameters for the reference object and the test biological object, and then using the distance between said points to determine the deviation of quantitative parameters that characterize the condition of the biological object under study from the quantitative parameters that characterize the reference object, characterized in that the reference object used in the method is made of a non-biological material, the fixation of the structure of gas-discharge light emission around the reference object is performed multiple times, the relative deviation $\delta$ a value in the series of measured quantitative parameters of structures of gas-discharge light emission around the reference object from their average value is calculated, and at $\delta \leq 10\%$ the structures of gas-discharge light emission around the reference and the test biological objects are compared, whereas at $\delta > 10\%$ the output voltage of the electric pulse generator is reduced and/or the stability of said pulses is increased until obtaining $\delta \leq 10\%$.

2. A method as claimed in claim 1, characterized in that the reference object is made of metal.

3. A method as claimed in claim 1, characterized in that the reference object is embodied as a vessel with conductive liquid.

4. A device for determining the condition of a biological object, which comprises an electromagnetic pulse generator, a glass plate that has an electrode on the lower surface thereof in the form of a layer of a conductive optically transparent material, an objective lens, an optoelectronic digital converter, a computer unit, an information presentation unit, a switching device that allows connecting the generator in turn to the reference object or the biological object under study, wherein the first output of the generator is connected to the switching device and the second output of the generator is connected to the electrode, the output of the objective lens is optically connected to the optical input of the optoelectronic digital converter, and the first output of the computer unit is connected to the input of the information presentation unit, characterized in that the device additionally comprises a unit for calculating the relative deviation $\delta$ of a value in the series of measured quantitative parameters of structures of gas-discharge light emission around the reference object from their average value and a unit of logical decisions, wherein the input of the unit for calculating the relative deviation $\delta$ is connected to the first output of the optoelectronic digital converter, the second output of which is connected to the first input of the computer unit, the second input of which is connected to the first output of the unit of logical decisions, the second output of which is connected to the generator input.

5. A device for determining the condition of a biological object as claimed in claim 4, characterized in that the switching device is embodied as an electronic or electromechanical switch.

* * * * *